(12) United States Patent
Prakash et al.

(10) Patent No.: US 7,119,232 B2
(45) Date of Patent: Oct. 10, 2006

(54) NUCLEOPHILIC SUBSTITUTION REACTIONS OF DIFLUORORMETHYL PHENYL SULFONE WITH ALKYL HALIDES LEADING TO THE FACILE SYNTHESIS OF TERMINAL 1,1-DIFLUORO-1-ALKENES AND DIFLUOROMETHYLALKANES

(75) Inventors: G. K. Surya Prakash, Hacienda Heights, CA (US); Jinbo Hu, Shanghai (CN); George A. Olah, Beverly Hills, CA (US); Ying Wang, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 11/086,723

(22) Filed: Mar. 22, 2005

(65) Prior Publication Data

US 2006/0052643 A1    Mar. 9, 2006

Related U.S. Application Data

(60) Provisional application No. 60/556,508, filed on Mar. 26, 2004.

(51) Int. Cl.
C07C 317/14    (2006.01)
(52) U.S. Cl. ....................................................... 568/24
(58) Field of Classification Search ................... 568/24
See application file for complete search history.

(56) References Cited

U.S. PATENT DOCUMENTS 4,837,327 A * 6/1989 Stahly .......................... 546/24

OTHER PUBLICATIONS

Prakash et al., Nucleophilic Difluoromethylation of Primary Alkyl Halides Using Difluoromethyl Phenyl Sulfone as a Difluoromethyl Anion Equivalent, Org. Lett.; (Letter); 2004; 6(23); 4315-4317.*
Prakash et al., Difluoromethyl Phenyl Sulfone, a Difluoromethylidene Equivalent: Use in the Synthesis of 1, 1-Difluoro-1-alkenes (p. 5203-5206), Angew. Chem. Int. Ed. 2004, 43, 5203-5206.*

G. Patrick Stahly, "Nucleophilic addition of difluoromethyl phenyl sulfone to aldehydes and various transformations of the resulting alcohols," Journal of Fluorine Chemistry, 43: 53-66 (1989).

* cited by examiner

Primary Examiner—Johann Richter
Assistant Examiner—Chukwuma Nwaonicha
(74) Attorney, Agent, or Firm—Winston & Strawn LLP

(57) ABSTRACT

(Benzenesulfonyl)difluoromethyl anion, in situ generated from difluoromethyl phenyl sulfone and a base, was found to easily undergo nucleophilic substitution reactions ($S_N2$) with primary alkyl halides, elemental halogens, and perfluoroalkyl halides with good selectivity. The formed (benzenesufonyl)difluoromethylalkanes are useful intermediates for the facile preparation of 1,1-difluoro-1-alkenes and difluoromethylalkanes. Thus, difluoromethyl phenyl sulfone acts as both "$CF_2=$" and "$CF_2H^-$" synthons

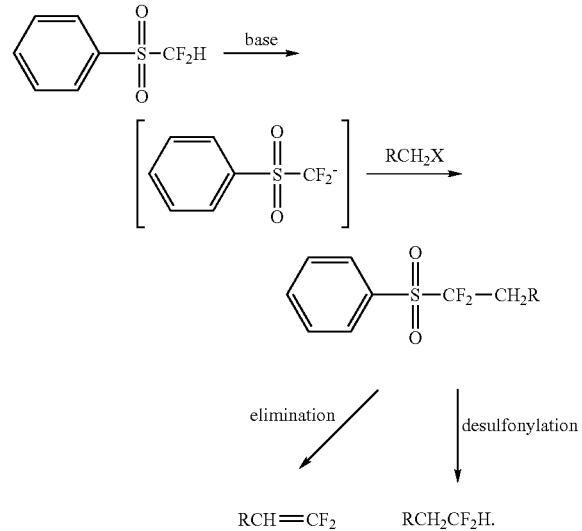

17 Claims, No Drawings

NUCLEOPHILIC SUBSTITUTION REACTIONS OF DIFLUORORMETHYL PHENYL SULFONE WITH ALKYL HALIDES LEADING TO THE FACILE SYNTHESIS OF TERMINAL 1,1-DIFLUORO-1-ALKENES AND DIFLUOROMETHYLALKANES

This application claims the benefit of provisional application No. 60/556,508 filed Mar. 26, 2004.

BACKGROUND

The selective introduction of fluorine atoms into organic molecules is of great interest, due to the broad applications of fluorine-containing compounds in pharmaceutical and agricultural chemistry, and material science.[1] Recently, two classes of gem-difluoro compounds have attracted much attention: 1,1-difluoro-1-alkenes and difluoromethylalkanes.[2] 1,1-Difluoro-1-alkene functionality has been known to act as a bioisostere for aldehydes and ketones,[3] and it is critical to many biologically active molecules such as enzyme inhibitors,[4] and pesticides.[5] 1,1-Difluoro-1-alkenes are also useful synthetic precursors for the preparation of many other fluorinated compounds and polymers.[6] A number of examples of the preparation of 1,1-difluoro-1-alkenes have been documented in the literature, mostly relying on the addition of a reagent that adds the terminal carbon or the terminal two or three carbons containing the two fluorines to an electrophile or a nucleophile.[2a,6-8] The most common method is the Wittig reaction using difluoromethylene ylides.[7] However, these methods either need specialized procedures or hard-to-handle reagents, which limits their generality for the functional group transformations. Difluoromethyl functionality ($CF_2H$) has been known to be isosteric and isopolar to the hydroxyl group, and it behaves as a hydrogen donor through hydrogen bonding.[9,10] Moreover, $CF_2H$ group has the similar high lipophilicity as the trifluoromethyl group. All these special properties make $CF_2H$ functionality a desired moiety to be incorporated into the organic molecules in order to enhance the their biological activities.[11] Many functionalized difluoromethylalkanes have been applied in various fields such as pesticides,[12] enzyme inhibitors,[13] liquid crystals,[14] and fluoropolymers.[15] However, only a limited number of methods have been developed for the preparation of difluoromethylalkanes, including the deoxofluorination of aldehydes using $SF_4$, DAST or $SeF_4$,[16] nucleophilic fluorination of gem-bistriflates using TBAF,[17] fluorination of 1,2- or 1,3-dithiane using $BrF_3$ and other in situ generated halogen fluorides,[2e,18] and the addition of dibromodifluoromethane to double bonds.[19] Most of these methods need the unpleasant reagents such as $SF_4$, HF and their derivatives, with poor toleration of other functional groups on substrates. Thus, the new development of a general, mild and efficient synthetic method to selectively introduce 1,1-difluoro-1-alkene and difluoromethyl moieties into widely available organic substrates is of much importance.

Alky halides, such as alkyl iodides or bromides, are a group of easily available compounds, either from commercial sources or through the easy transformations from other compounds such as alcohols.[20] Alkyl halides have been extensively used to form new carbon-carbon bonds due to the high reactivity of carbon-halogen bonds.[21] However, little has been known about the selective carbon-carbon bond formation between a fluorinated carbon atom and the carbon atom of a simple aliphatic alkyl halide. The carbon-carbon bond formations between "$C_nF_{2n+1}^-$" species with aromatic, and some particular alkyl halides (such as benzylic, allylic or propargylic alkyl halides) have been reported, using fluorine-containing organocopper ($R_fCu$) species.[22a-b,18b] But the reaction usually does not work efficiently for other types of alkyl halides, which only affords low to moderate yields of products.[22c-e] Therefore, the selective and efficient carbon-carbon bond formation between a fluorinated carbon species and a simple alkyl halide (non-benzylic, non-allylic, non-propargylic) still remains a challenge.

The possible solution to this difficult problem is to introduce a proper auxiliary functional group connecting to the fluorinated carbon nucleophile to increase its softness, since the alkyl halide is a soft electrophile. Furthermore, the proper auxiliary group should be easily removed or transformed into other functional groups afterwards. Benzenesulfonyl group [$PhS(O)_2$—] is one of the choices, for its softness and its varying chemical reactivities (so-called "chemical chameleon").[23,24] Difluoromethyl phenyl sulfone 1 is the ideal compound for this purpose, due to its easy generation of (benzensufonyl)difluoromethide 2 after the deprotonation of its acidic proton of $CF_2H$ group (Scheme 1).[25-27] Difluoromethyl phenyl sulfone can be readily prepared from sodium thiophenoxide and chlorodifluoromethane followed by a simple oxidation.[25-28] The nucleophilic addition of 1 with carbonyl compounds in the presence of a base has been demonstrated.[26,27] Recently, we reported the synthetic application of 1 as a nucleophilic difluoromethylating agent[29] as well as a selective difluoromethylenating agent[27] for the diasteroselective synthesis of anti-2,2-difluoropropane-1,3-diols. However, the nucleophilic reaction of 1 (or 2) with alkyl halides is still unknown. Based on the above-mentioned mechanistic considerations, herein, we wish to report the unprecedented successful necleophilic substitution reactions of difluoromethyl phenyl sufone with primary alkyl halides (especially alkyl iodides), which allows us to accomplish the facile and efficient synthesis of 1,1-difluoro-1-alkenes and difluoromethylalkanes.

Scheme 1. Generation of (Benzenesulfonyl)difluoromethylide from Difluoromethyl Phenyl Sulfone and a Base

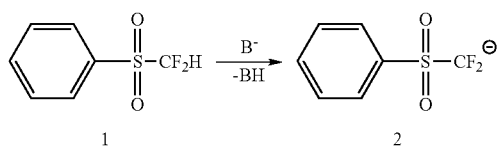

SUMMARY OF THE INVENTION

The invention relates to a method for preparing a (benzenesulfonyl)difluoroalkyl compound which comprises reacting difluoroalkylphenyl sulfone and a base under conditions sufficient to form a (benzenesulfonyl)difluoroalkyl anion, and further reacting the (benzenesulfonyl)difluoroalkyl anion with a nucleophile under conditions sufficient for the anion to undergo nucleophilic substitution and form the (benzenesulfonyl)difluoroalkyl compound.

Preferably, the base is an alkali or alkaline earth alkoxide, and the anion forming reaction is conducted in a solvent such as N,N-dimethylformamide or an organic solvent that has solvation properties that are functionally equivalent to N,N-dimethylformamide with the anion forming reaction conducted at a temperature of −80 to 0° C. A preferred nucleophile is an alkyl halide, halogen, or perfluoroalkyl halide so that the (benzenesulfonyl)difluoroalkyl that is formed is a (benzenesulfonyl)difluoroalkylalkane or (benzenesulfonyl)difluoroalkyl halides, respectively.

When the nucleophile is an alkyl halide, the (benzenesulfonyl)difluoroalkyl compound that is formed is a (benzenesulfonyl)difluoroalkylalkane. Preferred alkyl halides include an alkyl bromide, an alkyl iodide or an alkyl triflate wherein the alkyl group has 1 to 24 carbon atoms. The (benzenesulfonyl)difluoroalkylalkane may be subjected to desulfonylation under conditions sufficient to form a difluoroalkylalkane, or subjected to elimination of the benzenesulfonyl group under conditions sufficient to obtain a difluoroalkene. The reaction conditions generally include conducting the reaction in the presence of an alkoxide in a solvent at a temperature of between −20 and 0° C. with the solvent being tetrahydrofuran or an organic solvent that has solvation properties that are functionally equivalent to tetrahydrofuran.

When the nucleophile is a halogen, the (benzenesulfonyl)difluoroalkyl compound that is formed is a (benzenesulfonyl)difluoroalkyl halide. This compound can then be subjected to desulfonylation under conditions sufficient to form a difluoroalkyl halide. When the nucleophile is a perfluoroalkyl halide, the (benzenesulfonyl)difluoroalkyl compound that is formed is a (benzenesulfonyl)perfluoroalkyl halide.

If desired, the benzenesulfonyl ring of these compounds can be substituted with a moiety that will maintain the aromatic nature of the benzene ring and not cause cleavage of the benzene ring from the sulfonyl group during the reaction., such as a straight chain, branched or cyclic alkyl group having one to twelve carbon atoms. As this group is removed it is not critical to complicate it with the addition of different substituents.

DETAILED DESCRIPTION OF THE PREFERRED EMBODIMENTS

The first step of the reaction is to obtain sulfone substituted anions. Difluoroalkyl sulfones can be converted to difluoroalkyl sulfone anions by reaction with a base. Particular sulfones include various aryl difluoroalkyl sulfones This reaction is conducted in a solvent at a suitable temperature to facilitate the conversion.

The nucleophilic substitution of these sulfone anions with alkyl halides can produce new alkylated difluoroalkyl sulfones. Various alkyl halides can be used, but the primary alkyl iodides are preferred. These can also be substituted with phenyl, phenoxy or other groups to form interesting sulfones. Primary alkyl bromides are also suitable for the reaction but with somewhat lower yields being achieved. The yields from these reactions ranges from around 30 to 85%. Generally, about 3–6 equivalents of alkyl halide are used with about 1.5 to 4 equivalents of alkoxide per equivalent of sulfone.

The reaction proceeds under various conditions with the specific conditions being easily determinable by a skilled artisan. Preferably, the reaction is conducted under an inert atmosphere such as argon. A solvent such as dimethylformamide (DMF) or equivalent can be used and into which is introduced the alkoxide base. Both the base and solvent are preferably liquids at the reaction temperature, which is typically below 0° C. to as low as −80° C.

The preferred bases are alkyl-OK compounds, whereas the alkyl group has between 1 and 20 and preferably between 3 and 10 carbon atoms in a preferably branched alkyl group, with t-butyl being the most preferred for the reactions shown in the examples. Bases such as lithium dialkylamides as well as lithium bis(trimethylsilyl)amides are also efficient for the deprotonation of difluoroalkyl sulfones.

Difluoroalkenes can be prepared by beta-elimination from difluoroalkyl sulfones. This reaction also proceeds under various conditions. For example, a solvent such as tetrahydrofuran (THF) or equivalent can be used and into which is introduced the alkoxide base. Both the base and solvent are preferably liquids at the reaction temperature, which is preferably between −20° C. and room temperature. Yields range from over 50 to between 80% and 90%.

Suitable nucleophiles for this reaction have the formula $R_2CH-X$ where X is a halide so that the (benzenesulfonyl)difluoroalkyl compound that is formed has the formula $R_2CH-CF_2-SO_2-Ph$ where each R is H or a straight or branched C1 to C24 alkyl provided that at least one R is other than H and Ph is a benzenesulfonyl ring that is optionally substituted with a moiety that will maintain the aromatic nature of the ring and not cause cleavage of the benzene ring from the sulfonyl group during the reaction. Preferred nucleophiles have the formula $RCH_2-X$ where X is a halide so that the (benzenesulfonyl)difluoroalkyl compound that is formed has the formula $R-CH_2-CF_2-SO_2-Ph$ where R is a straight or branched C1 to C24 alkyl and Ph is as noted above.

The preferred bases for these reactions are alkyl-OK compounds, whereas the alkyl group has between 1 and 20 and preferably between 3 and 10 carbon atoms in a preferably branched alkyl group, with t-butyl being the most preferred for the reactions shown in the examples. Bases such as lithium dialkylamides as well as lithium bis(trimethylsilyl)amides are also efficient for the deprotonation and elimination of the phenylsulfonyl moiety.

The desulfonylation reaction is preferably carried out in a sodium/mercury amalgam such as 5 percent sodium in mercury. The temperature can range from about −20 to 0° C. for about 30 to 60 minutes. Various difluoromethyl sulfones in high yields of about 80 to 90 percent are achieved. Furthermore, these reactions are highly selective.

In order to increase the yield of the reductive desulfonylation reaction, a buffering agent can be added to control pH. The buffering agent is one that can offset the in-situ generated strong base that otherwise would complicate the reaction. Various acid salts can be used although phosphates are preferred. The most preferred phosphate is sodium monohydrogenphosphate.

Results and Discussion (a) Nucleophilic Substitution Reactions ($S_N2$) of 1 and Alkyl Halides. The nucleophilic substitution of difluoromethyl phenyl sulfone 1 with alkyl bromides, alkyl iodides and alkyl triflates were examined, to produce alkylated difluoromethyl sulfone 4, with careful modifications of reaction conditions (Scheme 2). The reaction was typically performed under argon atmosphere, and a base was added into a mixture of 1 and 3. The reaction condition optimization data is shown in Table 1. Six factors have been optimized to increase the yields of the reactions: reactant ratio, reaction temperature, reaction time, solvent, choices of alkyl halide, and base. First of all, the reactant ratio (1:3:base) was tuned. For 1 equiv. of 1, excess amounts of base (2 equiv.) and alkyl halide (4 equiv.) were found to be beneficial for the optimum reaction yields (see runs 1~4). The reactions were rather facile, and low temperature (−50° C.) and short reaction time (commonly 1 hr.) are sufficient to complete the reactions. Higher reaction temperature will not only significantly increase the decomposition rate of the in situ generated (benzenesufonyl)difluoromethide into difluorocarbene,[25] but also increase the side reaction rate between the base and alkyl halides. Furthermore, DMF was found to be the best choice as solvent, compared with THF and $CH_2Cl_2$ (runs 6~8). Alkyl iodides showed better reactivity than alkyl bromides in the reactions (runs 5 and 6). The reactions worked quite well for primary alkyl iodides, but it failed with secondary alkyl iodide (run 9). Mechanistically, this is a typical sign for $S_N2$ reaction. Methyl triflate did not react with 1 to give the expected product (run 10). This is probably due to the fast reaction between DMF, alkyl triflate, and t-BuOK to form the dialkyl acetal of DMF.[30] When THF was used as a solvent, however, the reaction still did not prevail for methyl triflate run 11). Finally, t-BuOK was chosen as an ideal base. Other bases like NaOH (run 6), butyllithium, LDA were tried with no success.

Following the reaction condition optimizations, a variety of alkyl-substituted gem-difluoromethyl phenyl sulfones were prepared in good yields using 1 (1 equiv.), primary alkyl iodide (4 equiv.) and t-BuOK (2 equiv.) at −50° C. during the period of around 1 hour. The results are summerized in Table 2. Various alkyl iodides with different chain length were able to be substituted with (benzenesulfonyl)difluoromethide (in situ generated from 1) and t-BuOK (entries 1–6). Substituted alkyl iodides also behave in the similar way, which leads to the formation of structurally diverse gem-difluorinated sulfones (entries 7–12). Alkyl-substituted difluoromethyl sulfones themselves are a group of useful compounds used as non-linear optical materials.[31] The known available method for their preparation is by the α-fluorination of sulfoxides bearing α-hydrogens by molecular fluorine with low yields (10~20%).[32] Our current methodology possesses many advantages over the $F_2$-approach regarding the safety, cost and efficiency.

TABLE 2

Preparation of Substituted Difluoromethyl Sufones 4 from 1 (1 equiv.), alkyl iodides (4 equiv.) and t-BuOK (2 equiv.) in DMF at −50° C. for 1 hour

| entry | $RCH_2I$ | $RCH_2CF_2SO_2Ph$ (4) | yield (%)[a] |
|---|---|---|---|
| 1 | $CH_3(CH_2)_6I$ | $CH_3(CH_2)_6CF_2SO_2Ph$ (4a) | 79 |
| 2 | $CH_3(CH_2)_4I$ | $CH_3(CH_2)_4CF_2SO_2Ph$ (4b) | 80 |
| 3 | $CH_3(CH_2)_3I$ | $CH_3(CH_2)_3CF_2SO_2Ph$ (4c) | 84 |
| 4 | $CH_3(CH_2)_2I$ | $CH_3(CH_2)_2CF_2SO_2Ph$ (4d) | 73 |
| 5 | $CH_3CH_2I$ | $CH_3CH_2CF_2SO_2Ph$ (4e) | 62 |
| 6 | $CH_3I$ | $CH_3CF_2SO_2Ph$ (4f) | 42 |
| 7 | $Ph(CH_2)_3I$ | $Ph(CH_2)_3CF_2SO_2Ph$ (4g) | 71 |
| 8 | $Ph(CH_2)_4I$ | $Ph(CH_2)_4CF_2SO_2Ph$ (4h) | 52 |
| 9 | $Ph(CH_2)_5I$ | $Ph(CH_2)_5CF_2SO_2Ph$ (4i) | 59 |
| 10 | $Ph(CH_2)_6I$ | $Ph(CH_2)_6CF_2SO_2Ph$ (4j) | 50 |
| 11 | $Ph_2CH(CH_2)_2I$ | $Ph_2CH(CH_2)_2CF_2SO_2Ph$ (4k) | 37 |
| 12 | $PhO(CH_2)_3I$ | $PhO(CH_2)_3CF_2SO_2Ph$ (4l) | 71 |
| 13 | $PhO(CH_2)_4I$ | $PhO(CH_2)_4CF_2SO_2Ph$ (4m) | 60 |
| 14 | $CH_3(CH_2)_4Br$ | $CH_3(CH_2)_4CF_2SO_2Ph$ (4b) | 61 |

[a] Isolated Yield.

Scheme 2. Nucleophilic Substitution of 1 with Alkyl Halides and Triflates

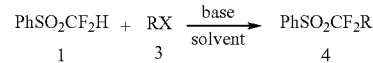

$$PhSO_2CF_2H + RX \xrightarrow[solvent]{base} PhSO_2CF_2R$$
$$1 \qquad\qquad 3 \qquad\qquad\qquad\qquad 4$$

TABLE 1

Reaction Condition Optimizations

| run | 1 (equiv.) | 3 (equiv.) | base (equiv.) | solvent | temperature (° C.) | time (h) | yield of 4 (%)[a] |
|---|---|---|---|---|---|---|---|
| 1 | 1.0 | n-$C_5H_{11}$Br (2.1) | t-BuOK (1.0) | DMF | −50~25 | 1.0 | 34 |
| 2 | 1.0 | n-$C_5H_{11}$Br (2.1) | t-BuOK (1.0) | DMF | −50~25 | 16.0 | 29 |
| 3 | 1.0 | n-$C_5H_{11}$Br (2.1) | t-BuOK (2.0) | DMF | −50~25 | 1.0 | 52 |
| 4 | 1.0 | n-$C_5H_{11}$Br (4.0) | t-BuOK (2.0) | DMF | −50 | 1.0 | 61 |
| 5 | 1.0 | n-$C_5H_{11}$I (4.0) | t-BuOK (2.0) | DMF | −50 | 1.0 | 85 |
| 6 | 1.0 | n-$C_5H_{11}$Br (10.0) | NaOH (25.0)[b] | $CH_2Cl_2$ | 25 | 20.0 | 0[c] |
| 7 | 1.0 | n-$C_2H_5$I (4.0) | t-BuOK (2.0) | DMF | −50 | 1.0 | 65 |
| 8 | 1.0 | n-$C_2H_5$I (4.0) | t-BuOK (2.0) | THF | −50 | 1.0 | 0[d] |
| 9 | 1.0 | 2-iodobutane (4.0) | t-BuOK (2.0) | DMF | −50 | 1.0 | 0[d] |
| 10 | 1.0 | $CF_3SO_3CH_3$ (4.0) | t-BuOK (2.0) | DMF | −50 | 1.0 | 0[e] |
| 11 | 1.0 | $CF_3SO_3CH_3$ (4.0) | t-BuOK (2.0) | THF | −50 | 1.0 | 0[e] |

[a] Yields were determined by $^{19}$F NMR using $PhOCF_3$ as internal standard;
[b] 50 wt. % aqueous NaOH solution was used, with the catalytic ammount of phase-transfer agent Aliquat 336;
[c] Unreacted 1 and small amount of byproduct $PhSO_2CF_2SPh$ were observed;
[d] A messy product mixture was observed;
[e] Starting material 1 was recovered.

(b) Related Reactions. In sharp contrast to normal alkyl iodides, perfluoroalkyl iodides can not undergo nucleophilic alkylation, because the electronegativities of the perfluoroalkyl groups are higher than that of iodine atom and thus nucleophiles attack at the iodine atom instead of the carbon atom.[1c] This principle also applies in the reaction where (benzenesulfonyl)difluoromethide was used as the nucleophile (Scheme 3). Instead of the perfluorinated long-chain sulfone ($PhSO_2C_7F_{15}$), the iodinated difluoromethyl sulfone 5 was formed in moderate yield. When elemental halogens such as $I_2$ and $Br_2$ were applied as electrophiles, corresponding iododifluoromethyl and bromodifluoromehtyl sulfones were produced (Scheme 4). The yield for bromination is lower than that of iodination, probably due to the fast rate of side reaction between bromine and t-BuOK.

Scheme 3. The Nucleophilic Substitution Reaction with Perfluoroalkyl Iodide

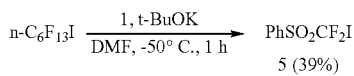

5 (39%)

Scheme 4. The Nucleophilic Substitution Reaction with Elemental Halogens

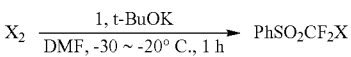

X = I, 5 (92%)
  = Br, 6 (38%)

Similarly, difluoromethyl phenyl sulfoxide 7 was used to react with alkyl iodide (Scheme 5). The corresponding alkyl-substituted difluoromethyl sufoxide 8 was formed in moderate yield, which indicates that (benzenesulfinyl)difluoromethide has the similar nucleophilicity as (benzenesulfonyl)difluoromethide.

Scheme 5. The Nucleophilic Substitution Reaction Using Difluoromethyl Phenyl Sulfoxide

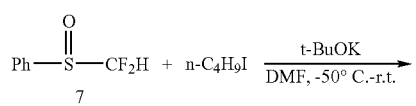

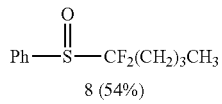

8 (54%)

(c) Facile Preparation of 1,1-Difluoro-1-Alkenes from 4. During the preparation of alkyl-substituted difluoromethyl sulfones 4 (Scheme 2), the formation of small amount of 1,1-difluoro-1-alkenes as the by-products was observed. This is due to the high acidity of the α-hydrogen of difluoromethylene group, which allows the easy deprotonation by t-BuOK to generate a new carbanion species 9 (Scheme 6). Intermediates 9 readily undergo β-elimination to eliminate the benzenesulfonyl group (rather than one fluorine atom) to afford 1,1-difluoro-1-alkenes 10, because the benzenesulfonyl group is known to be a better leaving group than the fluoride.[23] Thus, the one-pot preparation of 1,1-difluoro-1-alkenes is possible directly from alkyl iodides and 1 if much excess amount of t-BuOK is added. However, we found that the one-pot strategy is not practical especially when the purification is concerned. Since the excess amount of alkyl iodides (4 equiv.) were regularly applied for the reaction, the final separation between products 10 and extra alkyl iodides becomes problematic due to their similar physical properties. Hence, we prepared the 1,1-difluoro-1-alkenes 10 from the isolated substitution product 4 with t-BuOK in THF solution at −20° C. to ambient temperature. The deprotonation-β-elimination reactions proceeded rapidly (within 1 hour). Various 1,1-difluoro-1-alkenes were prepared in good to excellent yields by this method using the previously prepared sulfone compounds 4, as shown in Table 3. Therefore, the transformation from primary alkyl iodides to 1,1-difluoro-1-alkenes has accomplished in two steps via a substitution-elimination sequence. The advantage of this method is that the reactions are facile and straightforward, and more importantly, it only needs safe and inexpensive reagents and simple experimental procedures.

Scheme 6. The Formation of 1,1-Difluoro-1-Alkenes

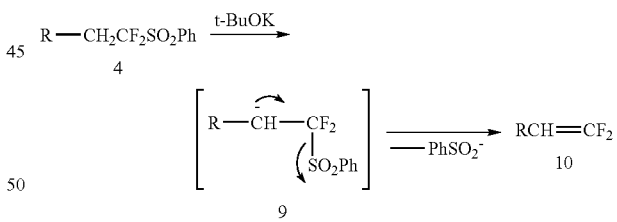

TABLE 3

Preparation of 1,1-Difluoro-1-alkenes 10 by Deprotonation-Elimination Reactions Using 4 and t-BuOK in THF Ranging from −20° C. to Room Temperature

| entry | $RCH_2CF_2SO_2Ph$ (4) | $RCH=CF_2$ (10) | yield (%)[a] |
|---|---|---|---|
| 1 | $Ph(CH_2)_3CF_2SO_2Ph$ | $Ph(CH_2)_2CH=CF_2$ (10a) | 85 |
| 2 | $Ph(CH_2)_4CF_2SO_2Ph$ | $Ph(CH_2)_3CH=CF_2$ (10b) | 71 |
| 3 | $Ph(CH_2)_5CF_2SO_2Ph$ | $Ph(CH_2)_4CH=CF_2$ (10c) | 82 |
| 4 | $Ph(CH_2)_6CF_2SO_2Ph$ | $Ph(CH_2)_5CH=CF_2$ (10d) | 80 |
| 5 | $Ph_2CH(CH_2)_2CF_2SO_2Ph$ | $Ph_2CHCH_2CH=CF_2$ (10e) | 84 |
| 6 | p-MeO—$C_6H_4$—$(CH_2)_4CF_2SO_2Ph$ | p-MeO—$C_6H_4$—$(CH_2)_3CH=CF_2$ (10f) | 55 |

TABLE 3-continued

Preparation of 1,1-Difluoro-1-alkenes 10 by Deprotonation-Elimination Reactions Using 4 and t-BuOK in THF Ranging from −20° C. to Room Temperature

| entry | $RCH_2CF_2SO_2Ph$ (4) | $RCH=CF_2$ (10) | yield (%)[a] |
|---|---|---|---|
| 7 | $PhO(CH_2)_3CF_2SO_2Ph$ | $PhO(CH_2)_2CH=CF_2$ (10g) | 88 |
| 8 | $PhO(CH_2)_4CF_2SO_2Ph$ | $PhO(CH_2)_3CH=CF_2$ (10h) | 87 |

[a]Isolated yield.

(d) Facile Preparation of Difluoromethyl Alkanes from 4. Reductive desulfonylation is widely used in the organic synthesis in order to remove the arenesulfonyl groups after the desired transformations.[23] After the desulfonylation, the arenesulfonyl groups are commonly replaced by a hydrogen atom. The reductive desulfonylations of gem-difluoro sulfones are scarce. (Benzenesulfonyl)difluoromethyl carbinols have been reductively desufonylated into difluoromethyl carbinols in low yields, using sodium metal in methanol.[26] Similar poor yields were obtained when we tried Na/MeOH system as desufonylating agents for the alkylated difluoromethyl sulfones 4. It was realized by us that the in situ generated strong base MeONa will further decompose the reaction products and thus decrease the desulfonylation efficiency. Inspired by the early report that the clean desulfonylation reaction can be obtained by applying a buffering agent to control the pH,[33] we added sodium monohydrogenphosphate ($Na_2HPO_4$) in our desufonylation reactions in order to selectively produce difluoromethyl alkanes (Scheme 7). Sodium/mercury amalgam (5 wt. % Na in Hg) was used, and the reactions were carried out at −20° C. to 0° C. for 0.5~1 hr. Various difluoromethyl alkanes were obtained from the corresponding alkylated difluoromethyl sulfones 4 in excellent yields (see Table 4). The reactions were highly selective that simplified the final purification processes.

Scheme 7. Preparation of Difluoromethylalkanes 11 by Desulfonylation of 4

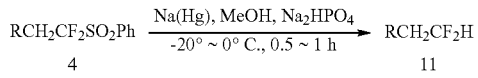

alkyl halides (especially alkyl iodides) have been developed, which demonstrates the efficient carbon-carbon bond formations between a fluorinated carbanion and simple alkyl halides. The similar types of substitution reactions with perfluoroalkyl iodides and elemental halogens have also been studied. The new alkyl-substitued difluoromethyl sulfones are highly useful compounds for their facile transformations into 1,1-difluoro-1-alkenes via base-induced eliminations, and difluoromethylalkanes through reductive desulfonylations. The new types of straightforward transformations from primary alkyl iodides into 1,1-difluoro-1-alkenes and difluoromethylalkanes provide the highly useful synthetic tools for many applications.

Experimental Section

Materials and Instrumentation. Unless otherwise mentioned, all other chemicals were purchased from commercial sources. Potassium t-butoxide (95%, Aldrich) was used as received. DMF was distilled over calcium hydride, and stored over activated molecular sieve. Difluoromethyl phenyl sulphone (1) was prepared using known procedures.[25,26,28] Some alkyl iodides were prepared from corresponding alkyl bromide (using NaI in acetone) or alcohols.[20] Silica gel column chromatography was used to isolate the products using 60–200 mesh silica gel (from J. T. Baker), mostly using hexane-ethyl acetate (9:1) as eluent. $^1H$, $^{13}C$ and $^{19}F$ NMR spectra were recorded on 500 MHz or 360 MHz NMR spectrometer. $^1H$ NMR chemical shifts were determined relative to internal $(CH_3)_4Si$ (TMS) at δ 0.0 or to the signal of a residual protonated solvent: $CDCl_3$ δ 7.26. $^{13}C$ NMR chemical shifts were determined relative to internal TMS at δ 0.0 or to the $^{13}C$ signal of solvent: $CDCl_3$ δ 77.0. $^{19}F$ NMR chemical shifts were determined relative to internal $CFCl_3$ at

TABLE 4

Preparation of Difluoromethylalkanes by Desulfonylations of 4 Using Na(Hg)/MeOH Ranging from −20° C. to 0° C.

| entry | $RCH_2CF_2SO_2Ph$ (4) | $RCH2CF_2H$ (11) | yield (%)[a] |
|---|---|---|---|
| 1 | $Ph(CH_2)_4CF_2SO_2Ph$ | $Ph(CH_2)_4CF_2H$ (11a) | 87 |
| 2 | $Ph(CH_2)_5CF_2SO_2Ph$ | $Ph(CH_2)_5CF_2H$ (11b) | 90 |
| 3 | $Ph(CH_2)_6CF_2SO_2Ph$ | $Ph(CH_2)_6CF_2H$ (11c) | 85 |
| 4 | $Ph_2CH(CH_2)_2CF_2SO_2Ph$ | $Ph_2CH(CH_2)_2CF_2H$ (11d) | 89 |
| 5 | $p\text{-MeO}—C_6H_4—(CH_2)_4CF_2SO_2Ph$ | $p\text{-MeO}—C_6H_4—(CH_2)_4CF_2H$ (11e) | 80 |
| 6 | $PhO(CH_2)_3CF_2SO_2Ph$ | $PhO(CH_2)_3CF_2H$ (11f) | 91 |
| 7 | $PhO(CH_2)_4CF_2SO_2Ph$ | $PhO(CH_2)_4CF_2H$ (11g) | 88 |

[a]Isolated yield.

Conclusions

The unprecedented nucleophilic substitution reactions ($S_N2$) of (benzenesulfonyl)difluoromethide (in situ generated from difluoromethyl phenyl sulfone and a base) with δ 0.0. GC-MS data were recorded on a GC-MS spectrometer with a mass selective detector at 70 eV. High-resolution mass data of low boiling compounds were recorded on a GC chromatograph with micromass GCT (time of flight) mass spectrometer. Other high-resolution mass data were recorded on a high-resolution mass spectrometer in the EI mode.

Typical Procedure for Nucleophilic Substitution Reactions of Difluoromethyl Phenyl Sulfone with Alkyl Iodides. Under an argon atmosphere, into a Schlenk flask containing difluoromethyl phenyl sulfone (192 mg, 1 mmol) and n-heptyl iodide (904 mg, 4 mmol) in DMF (4 mL) at −50° C., was added dropwise via a syringe t-BuOK (224 mg, 2 mmol) in DMF (4 mL). The reaction mixture was stirred at −50° C. for 1 h, and the completion of the reaction was monitored by $^{19}$F NMR. The reaction was then quenched by adding 1N HCl aqueous solution (5 mL) at −50° C., followed by warming to room temperature. A saturated NaCl aqueous solution (10 mL) was added, and the mixture was extracted with Et$_2$O (15 mL×3). The combined organic phase was dried over MgSO$_4$, filtered, and the solvent was removed in a rotary evaporator. The residue was further purified by silica gel column chromatography (hexane:ethyl acetate=9:1) to give 1,1-difluorooctyl phenyl sulfone (4a) (230 mg, 79% yield) as a colorless oily liquid. $^1$H NMR (500 MHz, CDCl$_3$): δ 0.88 (t, J=6.9 Hz, 3 H); 1.28 (m, 8 H); 1.64 (m, 2 H); 2.33 (m, 2H); 7.60 (t, J=8.3 Hz, 2H); 7.73 (t, J=7.3 Hz, 1H); 7.99 (d, J=7.9 Hz, 2H). $^{13}$C NMR (125 MHz, CDCl$_3$): δ 13.9; 20.7 (t, J=3.4 Hz); 22.4; 28.7; 29.0; 29.1; 31.4; 124.6 (t, J=286 Hz); 129.1; 130.6; 132.7; 135.1. $^{19}$F NMR (470 MHz, CDCl$_3$): δ −104.2 (t, J=19 Hz). GC-MS (EI, m/z): 291 (M$^+$+1); 142; 77. HRMS (EI): m/z calcd for C$_{14}$H$_{21}$F$_2$O$_2$S (M$^+$+H) 291.1230, found 291.1222.

1,1-Difluorohexyl Phenyl Sulfone (4b): colorless liquid, yield: 80%. $^1$H NMR (500 MHz, CDCl$_3$): δ 0.90 (t, 3H); 1.37 (m, 4H); 1.62 (m, 2H); 2.30 (m, 2H); 7.60 (t, 2H); 7.78 (t, 1H); 8.00 (2, 2H). $^{13}$C NMR (125 MHz, CDCl$_3$): δ 13.7; 20.4; 25.2; 29.1; 31.2; 124.7 (t); 129.2; 130.7; 132.5; 135.2. $^{19}$F NMR (470 MHz, CDCl$_3$): δ −104.6 (t, J=19 Hz). GC-MS (EI, m/z): 262 (M$^+$); 142; 77. HRMS (EI): m/z calcd for C$_{12}$H$_{17}$F$_2$O$_2$S (M$^+$+H) 263.0917, found 263.0904.

1,1-Difluoropentyl Phenyl Sulfone (4c): colorless liquid, yield: 84%. $^1$H NMR (500 MHz, CDCl$_3$): δ 0.93 (t, J=7.3 Hz, 2H); 1.42 (m, 2H); 1.62 (m, 2H); 2.32 (m, 2H); 7.60 (t, J=7.3 Hz, 2H); 7.74 (t, J=7.3 Hz, 1 H); 7.97 (d, J=7.9 Hz, 2H). $^{13}$C NMR (125 MHz, CDCl$_3$): δ 13.5; 22.3; 22.8 (t, J=3.5 Hz); 28.9 (t, J=20 Hz); 124.7 (t, J=286 Hz); 129.2; 130.7; 132.7; 135.1. $^{19}$F NMR (470 MHz, CDCl$_3$): δ 104.1 (t, J=19 Hz). GC-MS (EI, m/z): 248 (M$^+$); 142; 77. HRMS (EI): m/z calcd for C$_{11}$H$_{15}$F$_2$O$_2$S (M$^+$+H) 249.0761, found 249.0749.

1,1-Difluorobutyl Phenyl Sulfone (4d): colorless liquid, yield: 73%. $^1$H NMR (360 MHz, CDCl$_3$): δ 0.98 (t, J=7.2 Hz, 3H); 1.63 (m, 2H); 2.27 (m, 2H); 7.57 (t, J=7.8 Hz); 7.71 (t, J=7.6 Hz, 1H); 7.95 (d, J=7.7 Hz, 2H). $^{13}$C NMR (90 MHz, CDCl$_3$): δ 13.6; 14.4 (t, J=3.6 Hz); 30.9 (t, J=20 Hz); 124.5 (t, J=286 Hz); 129.2; 130.5; 132.4; 135.1. $^{19}$F NMR (338 MHz, CDCl$_3$): δ −104.1 (t, J=20 Hz). GC-MS (EI, m/z): 234 (M$^+$); 142; 77. HRMS (EI): m/z calcd for C$_{10}$H$_{12}$F$_2$O$_2$S (M$^+$+H) 235.0604, found 235.0597.

1,1-Difluoropropyl Phenyl Sulfone (4e): colorless liquid, yield 62%. $^1$H NMR (360 MHz, CDCl$_3$): δ 1.14 (t, J=7.2 Hz, 3H); 2.32 (m, 2H); 7.57 (t, J=7.7 Hz, 2H); 7.71 (t, J=7.6 Hz, 1H); 7.95 (t, J=7.8 Hz, 2H). $^{13}$C NMR (90 MHz, CDCl$_3$): δ 5.0 (t, J=4.2 Hz); 23.0; 124.6 (t, J=286 Hz); 129.2; 130.5; 132.4; 135.2. $^{19}$F NMR (338 MHz, CDCl$_3$): δ −106.1 (t, J=18 Hz). GC-MS (EI, m/z): 220 (M$^+$); 142; 77. HRMS (EI): m/z calcd for C$_9$H$_{10}$F$_2$O$_2$S (M$^+$) 220.0342, found 220.0381.

1,1-Difluoroethyl Phenyl Sulfone (4f): colorless liquid, yield 42%. $^1$H NMR (500 MHz, CDCl$_3$): δ 2.01 (t, J=19 Hz, 3H); 7.59 (t, J=7.9 Hz, 2H); 7.74 (t, J=7.6 Hz, 1H); 7.97 (d, J=7.9 Hz, 2H). $^{13}$C NMR (125 MHz, CDCl$_3$): δ 16.4 (t, J=22 Hz); 124.0 (t, J=283 Hz); 129.3; 130.7; 132.1; 135.3. $^{19}$F NMR (470 MHz, CDCl$_3$): δ −97.5 (q, J=19 Hz). GC-MS (EI, m/z): 206 (M$^+$); 142; 77. HRMS (EI): m/z calcd for C$_8$H$_8$F$_2$O$_2$S (M$^+$) 206.0213, found 206.0212.

1,1-Difluoro-4-phenylbutyl Phenyl Sulfone (4g): colorless liquid, yield 71%. $^1$H NMR (360 MHz, CDCl$_3$): δ 2.01 (m, 2H); 2.39 (m, 2H); 2.74 (t, J=7.5 Hz, 2 H); 7.21 (m, 3H); 7.32 (t, J=7.3 Hz, 2H); 7.62 (t, J=7.6 Hz, 2H); 7.76 (t, J=7.7 Hz, 1H); 8.00 (d, J=7.9 Hz, 2H). $^{13}$C NMR (90 MHz, CDCl$_3$): δ 22.5 (t, J=4 Hz); 28.6 (t, J=20 Hz); 35.0; 124.5 (t, J=286 Hz); 126.2; 128.3; 128.5; 129.2; 130.6; 132.3; 135.2; 140.5. $^{19}$F NMR (338 MHz, CDCl$_3$): δ −103.9 (t, J=19 Hz). MS (EI, m/z): 310 (M$^{10}$); 165; 149; 104. HRMS (EI): m/z calcd for C$_{16}$H$_{16}$F$_2$O$_2$S (M$^+$) 310.0839, found 310.0829.

1,1-Difluoro-5-phenylpentyl Phenyl Sulfone (4h): colorless liquid, yield: 52%. $^1$H NMR (360 MHz, CDCl$_3$): δ 1.73 (m, 4H); 2.38 (m, 2H); 2.67 (t, J=7.3 Hz, 2H); 7.19 (m, 3H); 7.30 (t, J=7.3 Hz, 2H); 7.62 (t, J=7.9 Hz, 2H); 7.76 (t, J=7.8 Hz, 1H); 7.99 (d, J=7.8 Hz, 2H). $^{13}$C NMR (90 MHz, CDCl$_3$): δ 20.5 (t, J=4 Hz); 29.0 (t, J=20 Hz); 30.9; 35.4; 124.6 (t, J=286 Hz); 125.9; 128.3; 128.4; 129.2; 130.7; 132.5; 135.2; 141.6. $^{19}$F NMR (338 MHz, CDCl$_3$): δ −104.1 (t, J=18 Hz).

1,1-Difluoro-6-phenylhexyl Phenyl Sulfone (4i): colorless thick liquid, yield: 59 %. $^1$H NMR (500 MHz, CDCl$_3$): δ 1.46 (m 2H); 1.69 (m, 4H); 2.36 (m, 2H); 2.65 (t, J=7.6 Hz, 2H); 7.21 (m, 3H); 7.31 (t, J=7.4 Hz, 2H); 7.62 (t, J=7.4 Hz, 2H); 7.76 (t, J=7.5 Hz, 1H); 8.01 (d, J=7.3 Hz, 2H). $^{13}$C NMR (125 MHz, CDCl$_3$): δ 20.6 (t, J=4 Hz); 28.6; 29.1 (t, J=18 Hz); 30.9; 35.5; 124.6 (t, J=286 Hz); 125.7; 128.2; 128.3; 129.2; 130.6; 132.4; 135.2; 142.1. $^{19}$F NMR (470 MHz, CDCl$_3$): δ −104.1 (t, J=18 Hz).

1,1-Difluoro-7-phenylheptyl Phenyl Sulfone (4j): colorless thick liquid, yield: 50%. $^1$H NMR (500 MHz, CDCl$_3$): δ 1.41 (m, 4H); 1.66 (m, 4H); 2.34 (m, 2H); 2.62 (t, J=7.3 Hz, 2H); 7.20 (m, 3H); 7.29 (t, J=7.3 Hz, 2H); 7.62 (t, J=7.5 Hz, 2H); 7.76 (t, J=7.3 Hz, 1H); 8.00 (d, J=7.5 Hz, 2H). $^{13}$C NMR (125 MHz, CDCl$_3$): δ 20.7 (t, J=4 Hz); 28.8; 29.0; 29.1 (t, J=20 Hz); 124.6 (t, J=286 Hz); 125.6; 128.2; 128.3; 129.2; 130.7; 132.5; 135.2; 142.5. $^{19}$F NMR (470 MHz, CDCl$_3$): δ −104.1 (t, J=19 Hz).

1,1-Difluoro-4,4-diphenylbutyl Phenyl Sulfone (4k): colorless oily liquid, yield: 37%. $^1$H NMR (500 MHz, CDCl$_3$): δ 2.37 (m, 2H); 2.49 (m, 2H); 4.02 (t, J=7.3 Hz, 1H); 7.23~7.36 (m, 10 H); 7.60 (t, J=7.4 Hz, 2H); 7.74 (t, J=7.5 Hz, 1H); 8.00 (d, J=7.4 Hz, 2H). $^{13}$C NMR (125 MHz, CDCl$_3$): δ 26.7; 28.2 (t, J=20 Hz); 50.6; 124.5 (t, J=286 Hz); 126.6; 127.6; 128.6; 129.2; 130.6; 132.3; 135.2; 143.3. $^{19}$F NMR (470 MHz, CDCl$_3$): δ −103.3 (t, J=19 Hz). MS (EI, m/z): 386 (M$^+$). HRMS (EI): m/z calcd for C$_{22}$H$_{20}$F$_2$O$_2$S (M$^+$) 386.1147, found 386.1148.

1,1-Difluoro-4-phenoxybutyl Phenyl Sulfone (4l): colorless oily liquid, yield: 71%. $^1$H NMR (360 MHz, CDCl$_3$): δ 2.17 (m, 2H); 2.61 (m, 2H); 4.04 (t, J=5.9 Hz); 6.92 (d, J=7.7 Hz, 2H); 7.00 (t, J=7.3 Hz, 1H); 7.31 (t, J=7.1 Hz, 2 H); 7.63 (t, J=7.1 Hz, 2 H); 7.77 (t, J=7.6 Hz, 1 H); 8.02 (d, J=8.0 Hz, 2H). $^{13}$C NMR (90 MHz, CDCl$_3$): δ 21.2 (t, J=3.7 Hz); 26.4; 66.1; 114.4; 120.9; 124.5 (t, J=286 Hz); 129.3; 129.4; 130.7; 132.3; 135.3; 158.5. $^{19}$F NMR (338 MHz, CDCl$_3$): δ −104.0 (t, J=18 Hz). MS (EI, m/z): 326 (M$^+$); 233; 185; 125. HRMS (EI): m/z calcd for C$_{16}$H$_{16}$F$_2$O$_3$S (M$^+$) 326.0788, found 326.0789.

1,1-Difluoro-5-phenoxypentyl Phenyl Sulfone (4m): colorless liquid, yield: 60%. $^1$H NMR (360 MHz, CDCl$_3$): δ 1.90 (m, 4H); 2.44 (m, 2H); 3.99 (t, J=5.8 Hz); 6.85~6.98 (m, 3H); 7.29 (t, J=7.5 Hz, 2H); 7.62 (t, J=7.6 Hz, 2H); 7.77 (t, J=7.6 Hz, 1H); 7.99 (d, J=7.6 Hz, 2H). $^{13}$C NMR (90

MHz, CDCl$_3$): δ 17.8 (t, J=3.6 Hz); 28.6; 28.9 (t, J=20 Hz); 66.8; 114.3; 120.6; 124.4 (t, J=286 Hz); 129.2; 129.3; 130.6; 132.3; 135.2; 158.7. $^{19}$F NMR (338 MHz, CDCl$_3$): δ −103.9 (t, J=18 Hz).

Typical Procedure for Nucleophilic Substitution Reactions of Difluoromethyl Phenyl Sulfone with Elemental Halogens. Under an argon atmosphere, into a Schlenk flask containing difluoromethyl phenyl sulfone (192 mg, 1 mmol) and elemental iodine (508 mg, 4 mmol) in DMF (4 mL) at −30° C., was added dropwise via a syringe t-BuOK (448 mg, 4 mmol) in DMF (4 mL). The reaction mixture was stirred at −30~−20° C. for 1 h, and the completion of the reaction was monitored by $^{19}$F NMR. The reaction was then quenched by adding 1N HCl aqueous solution (5 mL) at −50° C., followed by warming to room temperature. A saturated NaCl aqueous solution (10 mL) was added, and the mixture was extracted with Et$_2$O (15 mL×3). The combined organic phase was dried over MgSO$_4$, filtered, and the solvent was removed in a rotary evaporator. The residue was further purified by silica gel column chromatography (hexane:ethyl acetate=9:1) to give difluoroiodomethyl phenyl sulfone (5) (294 mg, 92% yield) as a colorless solid, which readily turns to red under light. $^1$H NMR (500 MHz, CDCl$_3$): δ 7.63 (t, J=7.4 Hz, 2H); 7.79 (t, J=7.4 Hz, 1H); 7.99 (d, J=7.5 Hz, 2H). $^{13}$C NMR (125 MHz, CDCl$_3$): δ 102.5 (t, J=355 Hz); 128.1; 129.7; 131.3; 136.1. $^{19}$F NMR (470 MHz, CDCl$_3$): δ −52.2. MS (EI, m/z): 318 (M$^+$); 177; 142; 127. HRMS (EI): m/z calcd for C$_7$H$_5$F$_2$IO$_2$S (M$^+$) 317.9023, found 317.9013.

Bromodifluoromethyl Phenyl Sulfone (6): light-sensitive colorless solid, yield: 38%. $^1$H NMR (360 MHz, CDCl$_3$): δ 7.67 (t, J=7.7 Hz, 2H); 7.84 (t, J=7.8 Hz, 1H); 8.04 (d, J=7.8 Hz, 2H). $^{19}$F NMR (338 MHz, CDCl$_3$): δ −58.0. MS (EI, m/z): 272 [M($^{81}$Br)$^+$]; 156; 141; 111. HRMS (EI): m/z calcd for C$_7$H$_5$BrF$_2$O$_2$S (M$^+$) 269.9162, found 269.9161.

Typical Procedures for the Preparation of 1,1-Difluoro-1-alkenes (10) from Alkyl-substitued Difluoromethyl Sulfones (4): Under an argon atmosphere, into a Schlenk flask containing 1,1-difluoro-4-phenylbutyl phenyl sulfone (4g) (100 mg, 0.32 mmol) in THF (4 mL) at −20° C., was added dropwise via a syringe t-BuOK (224 mg, 2 mmol) in DMF (4 mL). The reaction mixture was stirred at −20° C.~rt for 1 h, and the completion of the reaction was monitored by $^{19}$F NMR [δ −89.6 (d, J=46.6 Hz, 1F); −91.6 (dd, J=46.6 Hz, 24.8 Hz, 1F)]. The reaction was then quenched by adding aqueous NaCl solution (10 mL), followed by extraction with Et$_2$O (15 mL×3). The combined organic phase was dried over anhydrous Na$_2$SO$_4$, filtered, and the solvent was removed. The crude product was purified by a flash chromatography to give 1,1-difluoro-4-phenyl-1-butene (10a) (46 mg, 85% yield) as a colorless liquid. The characterization data is consistent with that early reported.[8h]

1,1-Difluoro-5-phenyl-1-pentene (10b): colorless liquid, yield: 71%. $^1$H NMR (360 MHz, CDCl$_3$): δ 1.70 (p, J=7.6 Hz, 2H); 2.01 (qt, J=7.5 Hz, 1.7 Hz, 2H); 2.62 (t, J=7.6 Hz, 2H); 4.15 (dtd, J=25 Hz, 7.9 Hz, 2.7 Hz, 1H); 7.16~7.31 (m, 5H). $^{13}$C NMR (90 MHz, CDCl$_3$): δ 21.8; 31.1; 35.1; 77.7 (t, J=21 Hz); 125.8; 128.3; 128.4; 142.0; 156.2 (t,J=286 Hz). $^{19}$F NMR (338 MHz, CDCl$_3$): δ −89.7 (d, J=46.6 Hz, 1F); −92.0 (dd, J=46.6 Hz, 25.1 Hz, 1F).

1,1-Difluoro-6-phenyl-1-hexene (10c): colorless liquid, yield: 82%. $^1$H NMR (360 MHz, CDCl$_3$): δ 1.43 (m, 2H); 1.66 (m, 2H); 2.03 (m, 2H); 2.63 (t, J=7.4 Hz, 2H); 4.14 (dtd, J=25.5 Hz; 7.8 Hz, 2.5 Hz, 1H); 7.18~7.34 (m, 5H). $^{13}$C NMR (90 MHz, CDCl$_3$): δ 22.0; 29.0; 30.7; 35.5; 77.8 (t, J=21 Hz); 125.7; 128.3; 128.4; 142.4; 156.3 (t, J=286 Hz). $^{19}$F NMR (338 MHz, CDCl$_3$): δ −90.0(d, J=50 Hz, 1F); −92.5 (dd, J=50 Hz, 25 Hz, 1F).

1,1-Difluoro-7-phenyl-1-heptene (10d): colorless liquid, yield: 80%. $^1$H NMR (360 MHz, CDCl$_3$): δ 1.40 (m, 4H); 1.64 (m, 2H); 1.99 (m, 2H); 2.62 (t, J=7.4 Hz, 2H); 4.13 (dtd, J=25 Hz, 7.9 Hz, 3.0 Hz, 1H); 7.17~7.33 (m, 5H). $^{13}$C NMR (90 MHz, CDCl$_3$): δ 22.1; 28.5; 29.3; 31.2; 35.9; 77.9 (t, J=21 Hz); 125.6; 128.3; 128.4; 142.6; 156.3 (t, J=286 Hz). $^{19}$F NMR (338 MHz, CDCl$_3$): δ −90.1(d, J=50 Hz, 1F); −92.5 (dd, J=50 Hz, 25 Hz, 1F).

1,1-Difluoro-4,4-diphenyl-1-butene (10e): colorless liquid, yield: 84%. $^1$H NMR (500 MHz, CDCl$_3$): δ 2.76 (m, J=7.7 Hz, 2H); 3.98 (t, J=7.9 Hz, 1H); 4.10 (dtd, J=25.4 Hz, 7.4 Hz, 2.6 Hz, 1H); 7.20~7.36 (m, 10 H). $^{13}$C NMR (125 MHz, CDCl$_3$): δ 28.5; 51.2; 76.6 (t, J=20 Hz); 126.5; 127.8; 128.5; 143.7; 156.3 (t, J=286 Hz). $^{19}$F NMR (338 MHz, CDCl$_3$): δ −88.8(d, J=46 Hz, 1F); −90.7 (dd, J=46 Hz, 24 Hz, 1F). MS (EI, m/z): 244 [M$^+$]. HRMS (EI): m/z calcd for C$_{16}$H$_{14}$F$_2$ (M$^+$) 244.1052, found 244.1053.

1,1-Difluoro-5-(4'-methoxy)phenyl-1-pentene (10f): colorless liquid, yield: 55%. $^1$H NMR (360 MHz, CDCl$_3$): δ 1.67 (m, 2H); 1.99 (m, 2H); 2.57 (t, J=7.4 Hz, 2H); 3.79 (s, 3H); 4.15 (dtd, J=25 Hz, 7.8 Hz, 3.0 Hz, 1H); 6.83 (d, J=8.6 Hz, 2H); 7.09 (d, J=8.5 Hz, 2H). $^{13}$C NMR (125 MHz, CDCl$_3$): δ 14.1; 21.7; 34.2; 55.2; 77.7 (t, J=21 Hz); 113.8; 129.3; 133.9; 156.3 (t, J=286 Hz); 157.8. $^{19}$F NMR (338 MHz, CDCl$_3$): δ −90.0(d, J=50 Hz, 1F); −92.3 (dd, J=50 Hz, 26 Hz, 1F).

1,1-Difluoro-4-phenoxy-1-butene (10g): colorless liquid, yield: 88%. $^1$H NMR (500 MHz, CDCl$_3$): δ 2.48 (m, 2H); 3.98 (t, J=6.2 Hz, 2H); 4.35 (dtd, J=25.4 Hz, 7.9 Hz, 2.4 Hz, 1H); 6.91 (d, J=8.0 Hz, 2H); 6.97 (t, J=7.5 Hz, 1H); 7.30 (t, J=8.0 Hz, 2H). $^{13}$C NMR (125 MHz, CDCl$_3$): δ 22.8; 66.7; 74.7 (t, J=22 Hz); 114.5; 120.9; 129.5; 156.8 (t, J=287 Hz); 158.7. $^{19}$F NMR (338 MHz, CDCl$_3$): δ −88.1 (d, J=46 Hz, 1F); −90.5 (dd, J=46 Hz, 26 Hz, 1F). MS (EI, m/z): 184 [M$^+$]. HRMS (EI): m/z calcd for C$_{10}$H$_{10}$F$_2$O (M$^+$) 184.0700, found 184.0702.

1,1-Difluoro-5-phenoxy-1-pentene (10h): colorless liquid, yield: 87%. $^1$H NMR (500MHz, CDCl$_3$): δ 1.87 (m, 2H); 2.21 (m, 2H); 3.97 (t, J=7.2Hz, 2H); 4.21 (dtd, J=25.4 Hz, 7.9 Hz, 2.4 Hz, 1H); 6.93 (m, 3H); 7.29 (t, J=7.5 Hz, 2H). $^{13}$C NMR (125 MHz, CDCl$_3$): δ 19.0; 29.0 (t, J=2.5 Hz); 66.6; 74.4 (t, J=22 Hz); 114.5; 120.7; 129.4; 156.4 (t, J=287 Hz); 159.0. $^{19}$F NMR (338 MHz, CDCl$_3$): δ −89.2 (d, J=46 Hz, 1F); −91.7 (dd,J=46 Hz, 26 Hz, 1F).

Typical Procedures for the Preparation of Difluoromethyl Alkanes (11) from Alkyl-substituted Difluoromethyl Sulfones (4): Under an argon atmosphere, into a Schlenk flask containing 1,1-difluoro-5-phenylpentyl phenyl sulfone (4h) (100 mg, 0.31 mmol), anhydrous Na$_2$HPO$_4$ (308 mg, 2.2 mmol) in methanol (4 mL) at −20° C., was added 5% Na/Hg amalgam beads (700 mg, ca. 1.5 mmol Na). The reaction mixture was stirred at −20° C.~0° C. for 1 h, and the completion of the reaction was monitored by $^{19}$F NMR. The methanol solution was decanted out, and the residue solids were washed with Et$_2$O (5 mL×3). The volatile solvents of the combined solution were removed under vacuum, and the crude product was purified by a flash chromatography to give 1,1-difluoro-5-phenylpentane (11a) (50 mg, 87% yield) as a colorless liquid. $^1$H NMR (500 MHz, CDCl$_3$): δ 1.51 (m, 2H); 1.70 (m, 2H); 1.86 (m, 2H); 2.64 (t, J=7.7 Hz, 2H); 5.80 (tt, J=57 Hz, 4.7 Hz, 1H); 7.19 (m, 3H); 7.30 (t, J=7.6 Hz, 2H). $^{13}$C NMR (125 MHz, CDCl$_3$): δ 21.7 (t, J=5.4 Hz); 30.8; 33.9 (t, J=21 Hz); 117.3 (t, J=239 Hz); 125.8; 128.3; 141.9. $^{19}$F NMR (470 MHz, CDCl$_3$): δ −116.2 (dt, J=57 Hz, 18 Hz, 1F).

1,1-Difluoro-6-phenylhexane (11b): colorless liquid, yield: 90%. ¹H NMR (360 MHz, CDCl₃): δ 1.40 (m, 2H); 1.49 (m, 2H); 1.66 (m, 2H); 1.82 (m, 2H); 2.63 (t, J=7.6 Hz, 2H); 5.79 (tt, J=57 Hz, 4.5 Hz, 1H); 7.20 (m, 3H); 7.29 (t, J=7.6 Hz, 2H). ¹³C NMR (90 MHz, CDCl₃): δ 21.9 (t, J=5.4 Hz); 28.6; 31.2; 34.0 (t, J=21 Hz); 35.7; 117.4 (t, J=239 Hz); 125.7; 128.3; 128.4; 142.4. ¹⁹F NMR (338 MHz, CDCl₃): δ −116.4 (dt, J=57 Hz, 18 Hz, 1F).

1,1-Difluoro-7-phenylheptane (11c): colorless liquid, yield: 85%. ¹H NMR (360 MHz, CDCl₃): δ 1.37 (m, 4H); 1.44 (m, 2H); 1.63 (m, 2H); 1.81 (m, 2H); 2.61 (t, J=7.5 Hz, 2H); 5.79 (tt, J=57 Hz, 4.5 Hz, 1H); 7.19 (m, 3H); 7.26 (t, J=7.5 Hz, 2H). ¹³C NMR (90 MHz, CDCl₃): δ 22.0 (t, J=5.5 Hz); 28.9; 29.0; 31.2; 34.0 (t, J=21 Hz); 35.8; 117.4 (t, J=239 Hz); 125.6; 128.2; 128.4; 142.6. ¹⁹F NMR (338 MHz, CDCl₃): δ −116.3 (dt, J=57 Hz, 18 Hz, 1F).

1,1-Difluoro-4,4-diphenylbutane (11d): colorless liquid, yield: 89%. ¹H NMR (500 MHz, CDCl₃): δ 1.80 (m, 2H); 2.23 (m, 2H); 3.94 (t, J=7.4 Hz, 1H); 5.83 (tt, J=57 Hz, 4.7 Hz, 1H); 7.24 (m, 10H). ¹³C NMR (125 MHz, CDCl₃): δ 27.7; 32.7 (t, J=21 Hz); 50.7; 117.1 (t, J=239 Hz); 126.6; 127.7; 128.6; 144.0. ¹⁹F NMR (470 MHz, CDCl₃): δ −116.2 (dt, J=57 Hz, 18 Hz, 1F). MS (EI, m/z): 246 [M⁺]. HRMS (EI): m/z calcd for C₁₆H₁₆F₂ (M⁺) 246.1215, found 246.1216.

1,1-Difluoro-5-(4'-methoxy)phenylpentane (11e): colorless liquid, yield: 80%. ¹H NMR (360 MHz, CDCl₃): δ 1.48 (m, 2H); 1.65 (m, 2H); 1.83 (m, 2H); 2.58 (t, J=7.5 Hz, 2H); 3,79 (s, 3H); 5.79 (tt,J=57 Hz, 4.5 Hz, 1H); 6.84 (d, J=8.0Hz, 2H); 7.08 (d, J=8.0Hz). ¹³C NMR (90 MHz, CDCl₃): δ 21.7 (t, J=5.5 Hz); 31.1; 34.0 (t, J=21 Hz); 34.7; 55.2; 113.8; 117.3 (t, J=239 Hz); 129.2; 134.0; 157.8. ¹⁹F NMR (338 MHz, CDCl₃): δ −116.2 (dt, J=57 Hz, 18 Hz, 1F).

1,1-Difluoro-4-phenoxybutane (11f): colorless liquid, yield: 91%. ¹H NMR (500 MHz, CDCl₃): δ 2.06 (m, 4H); 4.07 (t, J=7.4 Hz, 2H); 5.94 (tt, J=57 Hz, 4.7 Hz, 1H); 6.92 (d, J=7.5 Hz, 2H); 6.98 (t, J=7.4 Hz, 1H); 7.31 (t, J=7.5 Hz, 2H). ¹³C NMR (125 MHz, CDCl₃): δ 22.1 (t, J=5.9 Hz); 31.0 (t, J=21 Hz); 66.6; 114.4; 117.1 (t, J=239 Hz); 120.8; 129.5; 158.7. ¹⁹F NMR (470 MHz, CDCl₃): δ −116.6 (dt, J=57 Hz, 18 Hz, 1F). MS (EI, m/z): 186 [M⁺]. HRMS (EI): m/z calcd for C₁₀H₁₂F₂O (M⁺) 186.0856, found 186.0857.

1,1-Difluoro-5-phenoxypentane (11g): colorless liquid, yield: 88%. ¹H NMR (500 MHz, CDCl₃): δ 1.67 (m, 2H); 1.86 (m, 2H); 1.93 (m, 2H); 3.99 (t, J=7.4 Hz, 2H); 5.85 (tt, J=57 Hz, 4.7 Hz, 1H); 6.91 (d, J=7.5 Hz, 2H); 6.96 (t, J=7.4 Hz, 1H); 7.30 (t, J=7.5 Hz, 2H). ¹³C NMR (125 MHz, CDCl₃): δ 19.0 (t, J=5.9 Hz); 28.7; 33.8 (t, J=21 Hz); 67.2; 114.4; 117.2 (t, J=239 Hz); 120.7; 129.4; 158.9. ¹⁹F NMR (470 MHz, CDCl₃): δ −116.4 (dt, J=57 Hz. 18 Hz, 1F).

Acknowledgment: Support of our work by the Loker Hydrocarbon Research Institute is gratefully acknowledged.

REFERENCES (1) (a) *Organofluorine Chemistry: Principles and Commercila Applications*; Banks, R. E.; Tatlow, J. C.; Smart, B. E., Eds.; Plenum Press: New York, 1994. (b) McCarthy, J. *Utility of Fluorine in Biologically Active Molecules*, ACS Fluorine Division Tutorial, 219ᵗʰ National ACS Meeting, San Francisco, Mar. 26, 2000. (c) Hiyama, T., Eds. *Organofluorine compounds. Chemistry and Applications*, Springer: New York, 2000.

(2) (a) Ichikawa, J.; Fukui, H.; Ishibashi, Y. *J. Org. Chem.* 2003, 68, 7800. (b) Ichikawa, J.; Ishibashi, Y.; Fukui, H. *Tetrahedron Lett.* 2003, 44, 707. (c) Ichikawa, J.; Wada, Y.; Fujiwara, M.; Sakoda, K. *Synthesis* 2002, 1917. (d) Weintraub, P. M.; Holland, A. K.; Gates, C. A.; Moore, W. R.; Resvick, R. J.; Bey, P.; Peet, N. P. *Bioorg. Med. Chem.* 2003, 11, 427. (e) Sasson, R.; Hagooly, A.; Rozen, S. *Org. Lett.* 2003, 5, 769. (f)

(3) Motherwell, W. B. Jr.; Tozer, M. J.; Ross, B. C. *J. Chem. Soc., Chem. Comm.* 1989, 1437.

(4) (a) Moor, W. R.; Schatzman, G. L.; Jarvi, E. T.; Gross, R. S.; McCarthy, J. R. *J. Am. Chem. Soc.* 1992, 114, 360. (b) *Selective Fluorination in Organic and Bioorganic Chemistry*, ACS Symposium Series 456; Welch, J. T., Eds.; American Chemical Society: Washington, D.C., 1991.

(5) (a) Abe, T.; Tamai, R.; Tamaru, M.; Yano, H.; Takahashi, S.; Muramatsu, N., WO 2003042153, 2003; *Chem. Abstr.* 2003, 138, 401741. (b) Abe, T.; Tamai, R.; Ito, M.; Tamaru, M.; Yano, H.; Takahashi, S.; Muramatsu, N., WO 2003029211, 2003; *Chem. Abstr.* 2003, 138, 304304. (c) Fuji, K.; Hatano, Y.; Tsutsumiuchi, K.; Nakahon, Y., JP 2000086636, 2000; *Chem. Abstr.* 2000, 132, 222532.

(6) (a) Tozer, M. J.; Herpin, T. F. *Tetrahedron* 1996, 52, 8619. (b) Percy, J. M. *Contemp. Org. Synth.* 1995, 2, 251.

(7) (a) (a) Burton, D. J.; Naae, D. G. *J. Fluorine Chem.* 1971, 1, 123. (b) Burton, D. J.; Naae, D. G. *Synth. Commun.* 1973, 3, 197.

(8) (a) Matthews, D. P.; Miller, S. C.; Jarvi, E. T.; Sabol, J. S.; McCarthy, J. R. *Tetrahedron Lett.* 1993, 3057. (b) Bennett, A. J.; Percy, J. M.; Rock, M. H. *Synlett* 1992, 483. (c) Percy, J. M. *Tetrahedron Lett.* 1990, 31, 3931. (d) Tsukamoto, Kitazume, T. *Synlett*, 1992, 977. (e) Begue, J.-P.; Bonnet-Delpon, D.; Rock, M. H. *Tetrahedron Lett.* 1995, 36, 5003. (f) Shi, G.; Huang, X.; Zhang, F.-J. *Tetrahedron Lett.* 1995, 36, 6305. (g) Begue, J.-P.; Bonnet-Delpon, D.; Rock, M. H. *Tetrahedron Lett.* 1994, 35, 6097. (h) Kim, K.-I,; McCarthy, J. R. *Tetrahedron Lett.* 1996, 37, 3223. (j) Ichikawa, J. *J. Fluorine Chem.* 2000, 105, 257. (k) Brisdon, A. K.; Banger, K. K. *J. Fluorine Chem.* 1999, 100, 35. (l) Coe, P. L. *J. Fluorine Chem.* 1999, 100, 45.

(9) Yudin, A. K.; Prakash, G. K. S.; Deffieux, D.; Bradley, M.; Bau, R.; Olah, G. A. *J. Am. Chem. Soc.* 1997, 119, 1572; and the references therein.

(10) Erickson, J. A.; McLoughlin, J. I. *J. Org. Chem.* 1995, 60, 1626.

(11) Pu, Y. M.; Torok, D. S.; Ziffer, H.; Pan, X. Q.; Meshnick, S. R. *J. Med. Chem.* 1995, 38, 4120.

(12) (a) Otaka, K.; Oohira, D.; Takaoka, D., WO 2004006677, 2004. (b) Markl, M.; Schaper, W.; Ort, O.; Jakobi, H.; Braun, R.; Krautstrunk, G.; Sanft, U.; Bonin, W.; Stark, H.; Pasenok, S.; Cabrera, I., WO 2000007998, 2000; *Chem. Abstr.* 2000, 132, 166248.

(13) (a) Chen, Y.; Freskos, J. N.; Gasiecki, A. F.; Grapperhaus, M. L.; Hansen, D. W., Jr.; Heintz, R. M.; Khanna, I. K.; Kolodziej, S. A.; Mantegani, S.; Massa, M. A.; McDonald, J. J.; Mischke, D. A.; Nagy, M. A.; Perrone, E.; Schmidt, M. A.; Spangler, D. P.; Talley, J. J.; Trivedi, M.; Wynn, T. A.; Becker, D. P.; Rico, J. G., WO 2004000811, 2004; *Chem. Abstr.* 2004, 140, 59663. (b) Parker, M. F.; McElhone, K. E.; Mate, R. A.; Bronson, J. J.; Gai, Y.; Bergstrom, C. P.; Marcin, L. R.; Macor, J. E., WO 2003053912; *Chem. Abstr.* 2003, 139, 85645.

(14) Kondou, T.; Matsui, S.; Miyazawa, K.; Takeuchi, H.; Kubo, Y.; Takeshita, F.; Nakagawa, E., WO 9813324, 1998; *Chem. Abstr.* 1998, 128, 302171.

(15) *Fluorine-containing Molecules. Structure, Reactivity, Synthesis and Applications*, Liebman, J. F.; Greenberg, A.; Dolbier, W. R. Jr., Eds.; VCH: New York, 1988.

(16) (a) Middleton, W. J. *J. Org. Chem.* 1975, 40, 574. (b) Olah, G. A.; Nojima, M.; Kerekes, I. *J. Am. Chem. Soc.* 1974, 96, 925.

(17) Martinez, G. A.; Barcina, O. J.; Rys, A. Z.; Subramanian, L. R. *Tetrahedron Lett.* 1992, 33, 7787.

(18) (a) Sondej, S. C.; Katzenellenbogen, J. A. *J. Org. Chem.* 1986, 51, 3508. (b) *Synthetic Fluorine Chemistry*, Olah, G. A.; Chambers, R. D.; Prakash, G. K. S., Eds; Wiley: New York, 1992.

(19) Gonzales, J.; Foti, C. J.; Elsheimer, S. *J. Org. Chem.* 1991, 56, 4322.

(20) (a) Fernandez, I.; Garcia, B.; Munoz, S.; Pedro, J. R.; de la Salud, R. *Synlett* 1993, 489. (b) Imamoto, T.; Matsumoto, T.; Kusumoto, T.; Yokoyama, M. *Synthesis* 1983, 460. (c) Kamal, A.; Ramesh, G.; Laxman, N. *Synth. Commun.* 2001, 31, 827.

(21) *Advanced Organic Chemistry*, $5^{th}$ Ed., Smith, M. B.; March, J., Eds.; Wiley: New York, 2001.

(22) (a) Urata, H.; Fuchikami, T. *Tetrahedron Lett.* 1991, 32, 91. (b) Burton, D. J.; Hartgraves, G. A.; Hsu, J. *Tetrahedron Lett.* 1990, 31, 3699. (c) Kobayashi, Y.; Yamamoto, K.; Kumadaki, I. *Tetrahedron Lett.* 1979, 42, 4071. (d) Carr, G. E.; Chambers, R. D.; Holmes, T. F. *J. Chem. Soc. Perkin Trans. I* 1988, 921. (e) Chen, Q.-Y.; Duan, J.-X. *Tetrahedron Lett.* 1993, 34, 4241.

(23) *Sulfones in Organic Synthesis*, Tetrahedron Organic Chemistry Series, volumn 10, Baldwin, J. E.; Magnus, P. D., Eds.; Pergamon: New York, 1993.

(24) (a) Trost, B. M.; Chadiri, M. R. *J. Am. Chem. Soc.* 1984, 106, 7260. (b) Trost, B. M. *Bull. Chem. Soc. Jpn.* 1988, 61, 107.

(25) Hine, J.; Porter, J. J. *J. Am. Chem. Soc.* 1960, 82, 6178.

(26) Stahly, G. P. *J. Fluorine Chem.* 1989, 43, 53.

(27) Prakash, G. K. S.; Hu, J.; Mathew, T.; Olah, G. A. *Angew. Chem. Int. Ed.* 2003, 42, 5216.

(28) Langlois, B. R. *J. Fluorine Chem.* 1988, 41, 247.

(29) Prakash, G. K. S.; Hu, J.; Olah, G. A. *J. Org. Chem.* 2003, 68, 4457.

(30) Mesnard, D.; Miginiac, L. *J. Organomet. Chem.* 1989, 373, 1.

(31) Wijekoon, W. M. K. P.; Wijaya, S. K.; Bhawalkar, J. D.; Prasad, P. N.; Penner, T. L.; Armstrong, N. J.; Ezenyilimba, M. C.; Williams, D. J. *J. Am. Chem. Soc.* 1996, 118, 4480.

(32) (a) Toyota, A.; Ono, Y.; Chiba, J.; Sugihara, T.; Kaneko, C. *Chem. Pharm. Bull.* 1996, 44, 703. (b) Chiba, J.; Sugihara, T.; Kaneko, C. *Chem. Lett.* 1995, 581.

(33) Trost, B. M.; Arndt, H. C.; Strege, P. E.; Verhoeven, T. R. *Tetrahedron Lett.* 1976, 17, 3477.

What is claimed is:

1. A method for preparing a (benzenesulfonyl)difluoroalkyl compound which comprises reacting difluoroalkylphenyl sulfone and a base under conditions sufficient to form a (benzenesulfonyl)difluoroalkyl anion, and further reacting the (benzenesulfonyl)difluoroalkyl anion with a nucleophile under conditions sufficient for the anion to undergo nucleophilic substitution and form the (benzenesulfonyl)difluoroalkyl compound.

2. The method of claim 1, wherein the base is an alkali or an alkaline earth alkoxide, and the anion forming reaction is conducted in a solvent.

3. The method of claim 2, wherein the solvent is N,N-dimethylformamide or an organic solvent that has solvation properties that are functionally equivalent to N,N-dimethylformamide and the anion forming reaction is conducted at a temperature of –80 to 0° C.

4. The method of claim 1, wherein the nucleophile is an alkyl halide, halogen, or perfluoroalkyl halide so that the (benzenesulfonyl)difluoroalkyl compound that is formed is a (benzenesulfonyl)difluoroalkylalkane, or (benzenesulfonyl)difluoroalkyl halides, respectively.

5. The method of claim 4, wherein the nucleophile is an alkyl halide, and the (benzenesulfonyl)difluoroalkyl compound that is formed is a (benzenesulfonyl)difluoroalkyl alkane.

6. The method of claim 5, wherein the alkyl halide is an alkyl bromide, an alkyl iodide or an alkyl triflate wherein the alkyl group has 1 to 24 carbon atoms.

7. The method of claim 6, wherein the (benzenesulfonyl)difluoroalkylalkane is subjected to reductive desulfonylation under conditions sufficient to form a difluoroalkylalkane.

8. The method of claim 6, wherein the nucleophile has the formula $R_2CH-X$, where X is a halide so that the (benzenesulfonyl)difluoroalkyl compound that is formed has the formula $R_2CH-CF_2-SO_2-Ph$ where each R is H or a straight or branched C1 to C24 alkyl provided that at least one R is other than H and Ph is a benzenesulfonyl ring that is optionally substituted with a moiety that will maintain the aromatic nature of the ring and not cause cleavage of the benzene ring from the sulfonyl group during the reaction.

9. The method of claim 6, wherein the nucleophile has the formula $RCH_2-X$, where X is a halide so that the (benzenesulfonyl)difluoroalkyl compound that is formed has the formula $RCH_2-CF_2-SO_2-Ph$ where R is a straight or branched C1 to C24 alkyl and Ph is a benzenesulfonyl ring that is optionally substituted with a moiety that will maintain the aromatic nature of the ring and not cause cleavage of the benzene ring from the sulfonyl group during the reaction.

10. The method of claim 6, wherein the (benzenesulfonyl)difluoroalkyl alkane is subjected to elimination of the benzenesulfonyl group under conditions sufficient to obtain a difluoroalkene.

11. The method of claim 10, wherein the reaction conditions include conducting the reaction in the presence of an alkoxide in a solvent at a temperature of between –20 and 0° C.

12. The method of claim 11, wherein the solvent is tetrahydrofuran or an organic solvent that has solvation properties that are functionally equivalent to tetrahydrofuran.

13. The method of claim 4, wherein the nucleophile is a halogen so that the (benzenesulfonyl)difluoroalkyl compound that is formed is a (benzenesulfonyl)difluoroalkyl halide.

14. The method of claim 13, wherein the (benzenesulfonyl)difluoroalkylalkane is subjected to desulfonylation under conditions sufficient to form a difluoroalkyl halide.

15. The method of claim 4, wherein the nucleophile is a perfluoroalkyl halide so that the (benzenesulfonyl)difluoroalkyl compound that is formed is a (benzenesulfonyl)difluoroalkyl halide.

16. The method of claim 1, wherein the benzenesulfonyl ring is substituted with a moiety that will maintain the aromatic nature of the benzene ring and not cause cleavage of the benzene ring from the sulfonyl group during the reaction.

17. The method of claim 16, wherein the benzenesulfonyl ring is substituted with a straight chain, branched or cyclic alkyl group having one to twelve carbon atoms.

* * * * *